United States Patent
Wennogle

(10) Patent No.: US 9,339,500 B2
(45) Date of Patent: May 17, 2016

(54) METHODS OF TREATING VASOMOTOR SYMPTOMS

(75) Inventor: Lawrence P. Wennogle, New York, NY (US)

(73) Assignee: INTRA-CELLULAR THERAPIES, INC., New York, NY (US)

( * ) Notice: Subject to any disclaimer, the term of this patent is extended or adjusted under 35 U.S.C. 154(b) by 297 days.

(21) Appl. No.: 12/920,964

(22) PCT Filed: Mar. 4, 2009

(86) PCT No.: PCT/US2009/001391
§ 371 (c)(1),
(2), (4) Date: Jan. 19, 2011

(87) PCT Pub. No.: WO2009/111031
PCT Pub. Date: Sep. 11, 2009

(65) Prior Publication Data
US 2011/0152288 A1    Jun. 23, 2011

Related U.S. Application Data

(60) Provisional application No. 61/033,708, filed on Mar. 4, 2008.

(51) Int. Cl.
| | | |
|---|---|---|
| *A61K 31/415* | (2006.01) | |
| *A61K 31/135* | (2006.01) | |
| *A61K 31/496* | (2006.01) | |
| *A61K 31/137* | (2006.01) | |
| *A61K 31/472* | (2006.01) | |
| *A61K 31/4184* | (2006.01) | |
| *A61K 31/497* | (2006.01) | |
| *A61K 31/343* | (2006.01) | |

(52) U.S. Cl.
CPC ............. *A61K 31/497* (2013.01); *A61K 31/135* (2013.01); *A61K 31/137* (2013.01); *A61K 31/343* (2013.01); *A61K 31/4184* (2013.01); *A61K 31/472* (2013.01); *A61K 31/496* (2013.01)

(58) Field of Classification Search
CPC   A61K 31/4184; A61K 31/497; A61K 31/343
USPC ................................. 514/393, 398
See application file for complete search history.

(56) References Cited

U.S. PATENT DOCUMENTS

| | | | |
|---|---|---|---|
| 3,577,424 A | 5/1971 | Ehrhart | |
| 3,819,706 A | 6/1974 | Mehta | |
| 3,885,046 A | 5/1975 | Mehta | |
| 3,905,994 A | 9/1975 | Metlesics | |
| 4,338,317 A | 7/1982 | Temple | |
| 4,613,600 A | 9/1986 | Gammans | |
| 4,943,590 A | 7/1990 | Boegesoe | |
| 5,116,852 A | 5/1992 | Gammans | |
| 5,358,970 A | 10/1994 | Ruff | |
| 5,427,798 A | 6/1995 | Ludwig | |
| 5,731,000 A | 3/1998 | Ruff | |
| 5,763,493 A | 6/1998 | Ruff | |
| 6,229,026 B1 | 5/2001 | Petersen | |
| 6,258,842 B1 | 7/2001 | Petersen | |
| 6,291,689 B1 | 9/2001 | Petersen | |
| 6,365,747 B1 | 4/2002 | Dall'Asta | |
| 6,407,267 B1 | 6/2002 | Rock | |
| 6,420,574 B2 | 7/2002 | Petersen | |
| 6,426,422 B1 | 7/2002 | Petersen | |
| 2004/0152710 A1 | 8/2004 | Deecher et al. | |
| 2004/0180879 A1 * | 9/2004 | Deecher et al. ............ | 514/225.8 |
| 2004/0259850 A1 | 12/2004 | Alves et al. | |
| 2005/0059654 A1 * | 3/2005 | Arneric et al. ................ | 514/220 |
| 2005/0118242 A1 | 6/2005 | Dudley et al. | |
| 2006/0019966 A1 * | 1/2006 | Deecher et al. .......... | 514/255.04 |
| 2006/0276416 A1 | 12/2006 | Sinclair et al. | |
| 2007/0015828 A1 | 1/2007 | Shah et al. | |

OTHER PUBLICATIONS

Carpenter et al., "Randomized, Double-Blind, Placebo-Controlled Crossover Trials of Venlafaxine for Hot Flashes After Breast Cancer", The Oncologist, vol. 12, pp. 124-135 (2007).
Deecher et al., "Alleviation of Thermoregulatory Dysfunction With the New Seratonin and Norepinephrine Reuptake Inhibitor Desvenlafaxine Succinate in Ovariectomized Rodent Models", Women's Health and Musculoskeletal Biology, Wyeth Research, pp. 1-30 (2006).
Fitzpatrick, "Menopause and Hot Flashes: No Easy Answers to a Complex Problem", Mayo Clinic Proc., vol. 79, pp. 735-737 (2004).
Loprinzi et al., "Phase III Comparison of Depomedroxyprogesterone Acetate to Venlafaxine for Managing Hot Flashes: North Central Cancer Treatment Group Trial N99C7", Journal of Clinical Oncology, vol. 24, No. 9, pp. 1409-1414 (2006).
Stearns et al., "Paroxetine Controlled Release in the Treatment of Menopausal Hot Flashes, A Randomized Controlled Trial", JAMA, vol. 289, No. 21, pp. 2827-2834 (2007).
Carpenter et al, Fertil Steril. vol. 97, 1399-1404 (2012).
De Lean et al, Mol. Pharmacol., vol. 21, 5-16 (1982).
Galli et al, J. Exp. Biol., vol. 198, 2197-2212 (1995).
Maswood et. al, Neuroendocrinology, vol. 84, 330-338 (2006).
Munson et al, Anal. Biochem., vol. 107, 220-239 (1980).
Nelson et al, JAMA, vol. 295, 2057-2071 (2006).
Owens et al, J. Pharm. Exper. Therapeutics, vol. 283, 1305-1322 (1997).
Qian et al, J. Neurosci., vol. 17, 45-57 (1997).
Singh, S., Chem. Rev., vol. 100, 925-1024 (2000).
Taylor et al, Drugs of the Future, vol. 12, 758-759 (1987).

* cited by examiner

*Primary Examiner* — San-Ming Hui
(74) *Attorney, Agent, or Firm* — Hoxie & Associates LLC

(57) ABSTRACT

The present invention relates to methods for treating, preventing or controlling vasomotor symptoms such as hot flashes comprising administering specific norepinephrine/serotonin reuptake inhibitors.

13 Claims, No Drawings

METHODS OF TREATING VASOMOTOR SYMPTOMS

CROSS REFERENCE TO RELATED APPLICATIONS

This application is a 35 U.S.C. §371 National Phase Application of International Application No. PCT/US2009/001391, filed Mar. 4, 2009, claiming priority to U.S. Provisional Application No. 61/033,708, filed Mar. 4, 2008, the contents of which are herein incorporated by reference in their entirety.

TECHNICAL FIELD

The present invention relates to the use of norepinephrine/serotonin reuptake inhibitors (NRI/SRI) for the treatment of vasomotor symptoms (VMS), e.g., hot flashes.

BACKGROUND OF THE INVENTION

Thermoregulation is a complex function which helps the body maintain a constant temperature by intercommunicating between the core body temperature (CBT), the central nervous system (CNS) and the peripheral vasculature. Dysfunctions of this system resulting in hypo- or hyperthermia may be caused by exogenous heat exposure or endogenous heat production. Endogenous heat production that causes vasomotor symptoms (VMS) such as hot flashes and night sweats has affected 60-80% of all women undergoing natural, chemical or surgical induced menopause. Although hot flashes are the most common symptom affecting many menopausal women, its physiology is still poorly understood today. Studies have attempted to correlate hot flashes to hormonal levels of estradiol, follicle-stimulating hormone and luteinizing hormone, but no relationship has been found. Nevertheless, the use of hormones such as estrogen, progestogens or androgens is known to be an effective way of reducing hot flashes. However, adverse effects such as increased risk of coronary heart disease, thromboembolism, stroke, dementia, and/or breast cancer caused by these hormones have led to a need for alternative therapies.

The use of antidepressants for the treatment of hot flashes has increased over the years. Although the physiology of hot flashes is poorly understood today, there is supportive evidence for the role of norepinephrine (NE) and serotonin (5-HT) in thermoregulation. In particular, studies have revealed an association of increased levels of norepinephrine in the preoptic hypothalamus in the brain to hot flashes. Although studies have shown effective use of various serotonin and norepinephrine reuptake inhibitors such as Paroxetine, Fluoxetine, Venlafaxine, Desvenlafaxine in the treatment of hot flashes, the down side is that patients frequently experience side effects such as dry mouth, decreased appetite, nausea, constipation and sleeplessness, particularly at high dosages. Given the complex functions of thermoregulation and the various adverse effects of the drugs currently available, it is therefore desirable to introduce other norepinephrine/serotonin reuptake inhibitors (NRI/SRI) useful in the treatment of hot flashes.

SUMMARY OF THE INVENTION

The present invention provides a method for treating, alleviating, preventing or controlling vasomotor symptoms comprising administering to a subject in need thereof a therapeutically affective amount of one or more norepinephrine/serotonin reuptake inhibitors (NRI/SRI) selected from a group consisting of nortriptyline, escitalopram, bupropion, nomifensine, nefazodone, hydroxynefazodone and mazindol in free or salt form.

In another embodiment, the invention provides a method for treating, preventing or controlling vasomotor symptoms comprising (a) administering to a subject in need thereof a therapeutically affective amount of one or more NRI/SRI selected from nortriptyline, escitalopram, bupropion, nomifensine, nefazodone, hydroxynefazodone and mazindol, in free or pharmaceutically acceptable salt form, and (b) further administering sequentially or simultaneously, at least one other adrenergic$_{\alpha 2}$ receptor antagonists in free or salt form. While studies have shown that adrenergic$_{\alpha 2}$ receptor agonists such as clonidine are effective in treating hot flashes by decreasing norepinephrine release and/or sympathetic activation, co-administration of a NRI/SRI with an adrenergic$_{\alpha 2}$ receptor antagonist surprisingly alleviates hot flashes.

In a further embodiment, the present invention further comprise administering sequentially or simultaneously, at least one the adrenergic$_{\alpha 2}$ receptor antagonist selected from a group consisting of atipamezole, 2-[2-(4-(2-methoxyphenyl)piperazin-1-yl) ethyl]-4,4-dimethyl-1,3-(2H, 4H)-isoquinolindione dihydrochloride (ARC 239 dihydrochloride), 2-[(4,5-dihydro-1H-imidazol-2-yl) methyl]-2,3-dihydro-1-methyl-1H-isoindole maleate (BRL 44408 maleat), BRL48962, BRL41992, SKF 104856, SKF 104078, MK912, 2-(2-ethyl-2,3-dihydro-2-benzofuranyl)-4,5-dihydro-1H-imidazole hydrochloride (efaroxan hydrochloride), 2-(1,4-benzodioxan-2-yl)-2-imidazoline hydrochloride (idazoxan hydrochloride), 2-(1-ethyl-2-indazoyl) methyl-1,4-benzodioxan hydrochloride (imiloxan hydrochloride), 17a-hydroxy-20a-yohimban-16β-carboxylic acid, methyl ester hydrochloride (rauwolscine hydrochloride), (8aR,12aS,13aS)-5,8,8a, 9,10, 11,12,12a, 13,13a-dechydro-3-methoxy-12-(ethylsulfonyl)-6H-isoquino[2,1-y] [1,6]naphthyridine hydrochloride (RS 79948 hydrochloride), 2-(2,3-dihydro-2-methoxy-1,4-benzodioxin-2-yl)-4,5-dihydro-1H-imidazole hydrochloride (RX 821002 hydrochloride), 8-[(2,3-dihydro-1,4-benzodioxin-2-yl) methyl]-1-phenyl-1,3,8-triazaspiro[4,5]decan-4-one (spiroxatrine), 17a-hydroxyyohimban-16a-carboxylic acid methyl ester hydrochloride (yohimbine hydrochloride), 2-[(2,3-dihydro-1,4-benzodioxin-2-yl) methyl]-1-ethyl-1H-imidazole, and combinations and pharmaceutically acceptable salts thereof.

In a further embodiment, said adrenergic receptor antagonist is an adrenergic$_{\alpha 2B}$ receptor antagonist selected from a group consisting of 2-(1-ethyl-2-imidazoyl) methyl-1,4-benzodioxan (imiloxan), 2-[(2,3-dihydro-1,4-benzodioxin-2-yl) methyl]-1-ethyl-1H-imidazole, 2-[2-[4-(2-methoxyphenyl)-1-piperazinyl]ethyl]-4,4-dimethyl-1,3 (2H, 4H)-isoquinolinedione (ARC 239), or a combination or a pharmaceutical salt thereof.

In yet another embodiment, the invention provides a pharmaceutical composition comprising one or more norepinephrine reuptake inhibitors (NRI) selected from a group consisting of nortriptyline, escitalopram, bupropion, nomifensine, nefazodone, hydroxynefazodone and mazindol, in racemic, enantiomeric, free or pharmaceutically acceptable salt form, in combination or association with a pharmaceutically acceptable diluent or carrier for use in the treatment of vasomotor symptoms, e.g., hot flashes.

In yet another embodiment, the invention provides any of the foregoing methods wherein said NRI/SRI's are in a composition (e.g., a pharmaceutical composition comprising an NRI/SRI in admixture with a pharmaceutically acceptable excipient or carrier).

In still another embodiment, the invention provides use of an NRI/SRI according to the present invention, in free or salt form, in the manufacture of a medicament for treating, preventing or controlling vasomotor symptoms.

DETAILED DESCRIPTION OF THE INVENTION

A salt for an NRI/SRI may be, for example, an acid-addition salt of a compound of the method of the present invention which is sufficiently basic, for example, an acid-addition salt with, for example, an inorganic or organic acid, for example hydrochloric, hydrobromic, sulphuric, phosphoric, trifluoroacetic, citric or maleic acid which affords a physiologically-acceptable cation, for example a salt with methylamine, dimethylamine, trimethylamine, piperidine, morpholine or tris-(2-hydroxyethyl)amine. A salt of a compound of the method of the present invention which is sufficiently acidic is an alkali metal salt, for example a sodium or potassium salt, an alkaline earth metal salt, for example a calcium or magnesium salt, an ammonium salt or a salt with an organic base which affords a physiologically-acceptable cation. The NRI/SRI's of the Invention are intended for use as pharmaceuticals, therefore pharmaceutically acceptable salts are preferred.

It is also to be understood that certain compounds of the invention can exist in solvated as well as unsolvated forms such as, for example, hydrated forms. It is to be understood that the invention encompasses all such solvated forms which possess norepeniphrine transport (NET) and/or serotonin transport (SERT) regulatory activity.

Particular values of variable groups are as follows. Such values may be used where appropriate with any of the definitions, claims or embodiments defined hereinbefore or hereinafter.

The term "vasomotor symptoms" include, but are not limited to hot flashes (flushes), insomnia, sleep disturbances, mood disorders, irritability, excessive perspiration, night sweats, fatigue and other similar symptoms caused by thermoregulatory dysfunction. The term "hot flash(es)" or "hot flush(es)" refers to an episodic disturbance of the body temperature leading to symptoms ranging from a warming sensation, intense heat on the upper body and face, redness, perspiration and sometimes followed by chills.

According to a further aspect of the invention, there is provided a method for treating, preventing or controlling vasomotor symptoms comprising a pharmaceutical composition which comprises one or more compounds selected from nortriptyline, escitalopram, bupropion, nomifensine, nefazodone, hydroxynefazodone and mazindol in free or pharmaceutically acceptable salt thereof, as defined hereinbefore, in association with a pharmaceutically-acceptable diluent or carrier. Said compositions may generally be prepared in a conventional manner, e.g., as described in Remington's Pharmaceutical Sciences, $17^{th}$ Edition, ed. Alfonoso R. Gennaro, Mack Publishing Company, Easton, Pa. (1985), using conventional excipients.

The compounds or compositions of the methods of the present invention may be administered orally, for example as a tablet or capsule, parenterally (including intravenous, subcutaneous, intramuscular, intravascular, intraperitoneoal or infusion) as a sterile solution, suspension or emulsion, topically as an ointment or cream or via rectal administration as a suppository.

A "therapeutically effective amount" refers to an amount of compounds (e.g., nortriptyline, escitalopram, bupropion, nomifensine, nefazodone, hydroxynefazodone and mazindol, in racemic, enantiomeric, free or pharmaceutically acceptable salt form) or compositions at specific dosages and for a specific amount of time, sufficient to treat, prevent, and/or ameliorate a disease or condition, e.g., vasomotor symptoms, particularly hot flashes.

The compounds or compositions of the methods of the present invention will normally be administered to a subject at a unit dose within the range 1-1000 mg/kg, and this normally provides a therapeutically-effective dose. Preferably a daily dose in the range of 1-100 mg/kg is employed. However the daily dose will necessarily be varied depending upon the host treated, the particular route of administration, and the severity of the illness being treated. In addition, varying hormone levels will also influence the amount of compounds or compositions required to treat the subject. Accordingly the optimum dosage may be determined by the practitioner who is treating any particular patient.

In certain embodiments, the amount of NRI/SRI's of the present invention effective for the treatment, alleviation and/or prevention of vasomotor symptoms is less than about 150 mg/day, preferably less than 100 mg/day, more preferably less than 75 mg/day, still preferably 37.5 mg/day, preferably, less than about 30 mg/day, even more preferably, less than about 25 mg/day, yet even more preferably, less than about 20 mg/day, less than about 15 mg/day, less than about 10 mg/day and less than about 5 mg/day.

The term "inhibitor" is intended to comprise any compound, e. g., antibody, small molecule, peptide, oligopeptide, polypeptide, or protein, preferably small molecule or peptide, that exhibits a partial, complete, competitive and/or inhibitory effect on mammalian, preferably the human norepinephrine reuptake or both serotonin reuptake and the norepinephrine reuptake, thus diminishing or blocking, preferably diminishing, some or all of the biological effects of endogenous norepinephrine reuptake or of both serotonin reuptake and the norepinephrine reuptake.

The term "norepinephrine/serotonin reuptake inhibitors" or "NRI/SRI" or "NRI/SRI's" refers to compounds or agents that decrease, diminish, or reduce or block, partially or completely, the uptake or reuptake of norepinephrine or serotonin or both, thereby altering the level of norepinephrine and/or serotonin in the central nervous system. The NRI/SRI of the invention may have more selectivity for one receptor than another. For example, NRI/SRI's of the invention may be more selective for norepinephrine receptors. The NRI/SRI's referred to in the present invention are not intended to exclude compounds or agents that possess inhibitory activities for other receptors such as dopamine receptors. Therefore, the NRI/SRI's of the present invention may have NRI, SRI and/or dopamine activities. Examples of NRI/SRI's of the present invention include, but not limited to, nortriptyline, escitalopram, bupropion, nomifensine, nefazodone, hydroxynefazodone and mazindol, in free or salt form. NRI/SRI's of the present invention are intended to cover racemic mixtures as well as the enanatiomeric, amorphous, crystalline, hydrate and/or solvate forms.

The term "pre-menopausal" or "premature menopause" means before the menopause. Both "premature menopause" and "artificial menopause" may refer to menopause that occurs as a result of, e.g., ovarian failure of unknown cause that may occur before age of 40. It may be associated with smoking, living at high altitude, or poor nutritional status. Artificial menopause may also result from oophorectomy, chemotherapy, radiation of the pelvis, or any process that impairs ovarian blood supply.

The term "peri-menopausal" means during the menopause.

The term "post-menopausal" means after the menopause.

The term "andropause" refers to a condition, state or disorder characterized by symptoms, including, but not limited to reduction in Leydig cell numbers and a decline in androgen production, occurring in men, generally after middle age. Andropausal men therefore may also experience symptoms including, but not limited to fatigue, insomnia, hot flushes, and sweating. Therefore, the current invention also anticipates use by naturally, chemically and/or surgically induced andropausal male.

The term "subject" includes a warm-blooded animal, including the human species and intends to include both the male or female gender unless otherwise indicated. The subject according to the current invention includes not only women of advanced age who have gone through menopause (postmenopausal), but also pre- or peri-menopausal female wherein menopause may be naturally, chemically and/or surgically induced (e.g., those who have undergone oophorectomy, hysterectomy, chemotherapy, radiation of the pelvis or those who have suppressed estrogen production such as those who have undergone long-term use of corticosteroids or suffer from Cushing's syndrome or gonadal dysgenesis).

Adrenergic$_{\alpha 2}$ receptor antagonists of the present invention is selected from a group consisting of antagonists of the adrenergic$_{\alpha 2A}$ receptor, adrenergic$_{\alpha 2B}$ receptor, adrenergic$_{\alpha 2C}$ receptor and adrenergic$_{\alpha 2D}$ receptor including, but are not limited to, atipamezole; 2-[2-(4-(2-methoxyphenyl) piperazin-1-yl) ethyl]-4,4-dimethyl-1,3-(2H, 4H)-isoquinolindione dihydrochloride (ARC 239 dihydrochloride); 2-[(4,5-dihydro-1H-imidazol-2-yl) methyl]-2,3-dihydro-1-methyl-1H-isoindole maleate (BRL 44408 maleat); BRL48962; BRL41992; SKF 104856; SKF 104078; MK912; 2-(2-ethyl-2,3-dihydro-2-benzofuranyl)-4,5-dihydro-1H-imidazole hydrochloride (efaroxan hydrochloride); 2-(1,4-benzodioxan-2-yl)-2-imidazoline hydrochloride (idazoxan hydrochloride); 2-(1-ethyl-2-indazoyl) methyl-1,4-benzodioxan hydrochloride (imiloxan hydrochloride); 17a-hydroxy-20a-yohimban-16β-carboxylic acid, methyl ester hydrochloride (rauwolscine hydrochloride); (8aR,12aS,13aS)-5,8,8a,9,10,11,12,12a,13,13a-dechydro-3-methoxy-12-(ethylsulfonyl)-6H-isoquino[2,1-y][1,6]naphthyridine hydrochloride (RS 79948 hydrochloride); 2-(2,3-dihydro-2-methoxy-1,4-benzodioxin-2-yl)-4,5-dihydro-1H-imidazole hydrochloride (RX 821002 hydrochloride); 8-[(2,3-dihydro-1, 4-benzodioxin-2-yl) methyl]-1-phenyl-1,3,8-triazaspiro[4,5]decan-4-one (spiroxatrine); 17a-hydroxyyohimban-16a-carboxylic acid methyl ester hydrochloride (yohimbine hydrochloride); and combinations and pharmaceutically acceptable salts thereof.

Preferably, the adrenergic receptor antagonist is an adrenergic$_{\alpha 2B}$ receptor antagonist, which include, but are not limited to, 2-ethyl-2-imidazoyl) methyl-1,4-benzodioxan (imiloxan), 2-[(2,3-dihydro-1,4-benzodioxin-2-yl) methyl]-1-ethyl-1H-imidazole, 2-[2-[4-(2-methoxyphenyl)-1-piperazinyl]ethyl]-4,4-dimethyl-1,3 (2H, 4H)-isoquinolinedione (ARC 239), or a combination or a pharmaceutical salt thereof.

According to a further aspect of the present invention there is provided a method of treatment of the human or animal body by therapy.

General Methods of Making and Administering Compounds of the Invention

Compounds:

The methods of making the compounds of the present invention are generally known in the art. For instance, nortriptyline hydrochloride salt is commercially available and may be purchased, e.g., from Sigma-Aldrich. Nortriptyline free base may therefore be readily prepared from nortriptyline hydrochloride salt by methods well known in the art. Escitalopram is disclosed and may be prepared as described in U.S. Pat. Nos. 4,943,590; 6,660,873; 6,229,026; 6,258,842; 6,291,689; 6,365,747; 6,407,267; 6,420,574; 6426,422. Bupropion is disclosed and may be prepared as described in U.S. Pat. Nos. 3,819,706; 3,885,046; 5,427,798; 5,731,000; 5,763,493; 5,358,970. Nomifensine may be prepared as described in U.S. Pat. No. 3,577,424. Nefazodone is disclosed and may be prepared as described in U.S. Pat. No. 4,338,317; D. P. Taylor, et al, "Nefazodone Hydrochloride," Drugs of the Future, 12(8) pp. 758-759 (1987); U.S. Pat. Nos. 4,338,317; 5,116,852. Hydroxynefazodone is disclosed and may be prepared as described in U.S. Pat. Nos. 6,586,437 and 4,613,600. Mazindol is disclosed and may be prepared as described in U.S. Pat. No. 3,905,994; and Satendra Singh, *Chem. Rev.* (2000) 100, 925-1024. The contents of each of the references cited herewith are incorporated by reference by their entirety.

Norepiniphrine Binding Assay:

Binding assay may be found in Owens et al., *J. Pharm. Exper. Therapeutics* (1997) 283:1305-1322, the contents of which is incorporated herein by reference in their entirety.

Tissue Sources.

Male Sprague-Dawley rats or guinea pigs are housed with food and water available ad libitum in an environmentally controlled animal facility. Animals are sacrificed by guillotine decapitation without anesthesia as approved by the Emory University Animal Use and Care Committee.

For the SERT, NET, 5-HT$_{2A}$ and muscarinic cholinergic binding studies, pooled rat frontal cortex (anterior to the hippocampus) is collected and stored at −80° C. until needed. Similarly stored rat hippocampus is used for the 5-HT$_{1A}$ receptor assays. Pooled whole guinea pig brain is used for the H$_1$ receptor assay. Human frontal and parietal cortex is pooled from six normal control brains obtained from the brain bank of the Emory University Alzheimer's Disease Research Center for use in the alpha-1 and alpha-2 receptor assays. Postmortem delay in these samples ranged from 6 to 11 hours, and none of the patients are treated with any medications at the time of death that are known to interact with alpha adrenergic receptors.

Samples are homogenized with a Polytron PT 3000 (Brinkmann; 20,000 rpm×12 seconds) in 30 volumes of their individual assay buffers (table 1) at 4° C., and centrifuged at 43,000×g for 10 min. The supernatants are decanted and resuspended in 30 volumes of buffer, homogenized, separated into several individual aliquots and centrifuged. For membrane pellets that are used in the 5-HT$_{2A}$, 5-HT$_{1A}$, alpha-1 and alpha-2 binding assays, the pellets following the second centrifugation were resuspended in 30 volumes of buffer and the suspensions are preincubated in an oscillating water bath at 37° C. for 10 min. After preincubation, these suspensions are recentrifuged at 43,000×g for 10 min, the supernatants are decanted and resuspended in 30 volumes of cold buffer, homogenized, separated into several individual aliquots and centrifuged. The resulting pellets are stored at −70° C. until assayed.

Stable transfection of human SERT (Qian et al., 1997↓) or human NET cDNA (Galli et al., 1995↓) into HEK-293 (human embryonic kidney) cells results in cell lines exhibiting high-affinity, Na$^+$-dependent transport of serotonin or norepinephrine with pharmacological properties identical with those of native membranes. Both cell lines are grown in ten tray Nunc cell factories (6,320 cm$^2$) to confluence in Dulbecco's modified Eagle's medium containing 10% fetal bovine serum supplemented with L-glutamine (2 mmol/l final concentration), penicillin (100 μg/ml) and 100 units/ml streptomycin in a humidified incubator at 37° C. containing 5% CO$_2$. The selecting antibiotic geneticin sulfate (250 μg/ml) is used during all growth phases. Membranes are harvested using 37° C. phosphate-buffered saline containing 0.53 mmol/l ethylenediaminetetraacetic acid, separated into aliquots, and centrifuged at 2000×g for 10 min. The supernatants are decanted and the pellets homogenized as described above.

General radioligand binding assay methods. Serial dilution of radioligands or competing drugs may be carried out in borosilicate glass tubes silanized with Prosil 28 (PCR Inc., Gainesville Fla.). Fresh competing drug is weighed out for each individual competition curve. All competing drugs are initially dissolved in 50% ethanol containing 5 mmol/l HCl at a drug concentration of 1 mg/ml. Subsequent serial dilutions are performed in silanized glass tubes in 5 mmol/l HCl and added as ½0th the final total volume of the assay tubes. This does not alter the pH of any of the buffer systems. Comparing the use of silanized glass tubes with polystyrene and polypropylene tubes, silanized glass tubes are preferable for preparing serial dilutions. The total incubation volumes and membrane protein concentrations of all assays are adjusted such that the free ligand concentration is at least 95% of the total ligand concentration. For all membrane binding assays, with the exception of those using human brain tissue which are not able to study, the $K_d$ values of freshly prepared tissue pellets and previously frozen tissue pellets are identical, although a 0 to 8% decrease in $B_{max}$ is observed among the various assays. Competition assays use 19 to 20 concentrations of competing ligand in triplicate over a maximum concentration range of $10^{-13}$ to $10^{-4.6}$ mol/l. The chosen concentrations of competing ligand are adjusted for each assay to provide at least 10 points on the curve between 10% and 90% displacement. The only exceptions are the transport and radioligand binding assays with the hSERT and hNET cell lines which use 12 concentrations of competing ligand. All competition binding assays use a single concentration of $^3$H-labeled radioligand equal to the calculated $K_d$ of that ligand for its receptor. Competitive transport assays use a single concentration of either [$^3$H]serotonin (final concentration 20 nmol/l; 5 nmol/l [$^3$H]serotonin, 15 nmol/l serotonin) or [$^3$H]norepinephrine (final concentration 20 nmol/l; 5 nmol/l [$^3$H]norepinephrine, 15 nmol/l (−)-norepinephrine).

Total and nonspecific binding is determined in triplicate at each concentration of ligand. All incubations are terminated by the addition of an excess of ice-cold assay buffer, vacuum filtration over Whatman GF/B filters (presoaked in buffer containing 0.3% polyethyleneimine) and washed four times with 5 ml of ice-cold buffer. Filters are dried and suspended in 10 ml of Aquasol (DuPont/New England Nuclear, Boston, Mass.) scintillation fluid and equilibrated for a minimum of 60 min before counting in a liquid scintillation counter at 50% efficiency.

For transport assays, HEK-293 cells stably transfected with either the hSERT cDNA or hNET cDNA are grown to confluence in Dulbecco's modified Eagle's medium as described above and plated out at a density of approximately 100,000 cells/well into poly-L-lysine (0.5 mg/ml)-coated 24-well culture plates. Cells are allowed to adhere to plates for 24 hr before use in the assay (Galli et al., *J. Exp. Biol.*, (1995) 198:2197-2212; Qian et al., *J. Neurosci.* (1997) 17:45-57). Wells are pre-incubated for 10 min with competing ligand before addition of radio-ligand. Incubations are terminated by the addition of 1 ml of buffer (pH 7.4, 22° C.), quickly aspirated and washed once with 1 ml of 37° C. buffer. Cells are removed from plates by the addition of 500 µl of 1% sodium dodecyl sulfate.

For each different receptor assay, the results of six separate saturation studies are simultaneously analyzed by use of the computer program LIGAND (Munson and Rodbard, *Anal. Biochem.* (1980) 107:220-239). In competition assays, the results of at least three separate competition assays are analyzed by use of the computer program PRISM 2.0 (GraphPad Software, Inc., San Diego, Calif.). In all instances, LIGAND or PRISM analysis revealed that the data are best fit by a one-site model rather than a two-site model. All $K_i$ data are expressed as geometric mean±S.E. in nanomoles per liter. Geometric means and S.E. are calculated by the method described by De Lean et al., *Mol. Pharmacol.* (1982) 21:5-16). p$K_i$ correlations were conducted by Pearson correlations with SAS software (Cary, N.C.). The result will indicate that the compounds of the present invention are selective for norepinephrine and/or serotonin transporters, particularly norepinephrine transporters.

Effectiveness of the Compounds of the Present Invention to Reduce Hot Flashes

The effectiveness of the compounds of the present invention to reduce hot flashes may be evaluated according to the procedure provided in Maswood et. al., *Neuroendocrinology* 84:330-338 (2006), the contents of which are herein incorporated by reference in their entirety.

Overiectomized Rat Model:

Ovariectomized female rats are housed on a 12-hour light/dark cycle. A telemetric transmitter is implanted in the dorsal scapular region of the rat and tip of the tunnel probe is inserted 2.5 cm beyond the base of the tail to measure the tail skin temperature (TST). For measurement of the core body temperature (CBT), a 3-4 cm long incision is made in the midline of the abdomen of the rats through the abdominal musculature and a transmitter is placed in the abdominal cavity. A vehicle is administered subcutaneously to the rat 0.5 h before the onset of the dark phase and TST is monitored continuously for 12 hours to establish the baseline. Twenty-four hours later, either vehicle or test compounds of the present invention are administered subcutaneously. TST is monitored for 12 hours. An average temperature is calculated for every 30-min time point. The change in temperature is calculated by taking the average temperature for each 30-min time point on the compound dosing day minus the overall average baseline temperature on vehicle dosing day (average temperature over 12 hours).

Morphine-Dependent Rat Model:

The effectiveness of the compounds of the present invention to reduce hot flashes is evaluated by measuring its ability to reduce morphine-induced rise in TST. Ovariectomized rats are subcutaneously injected with a vehicle (sterile water) once daily for 8 days. On day-4, two tablets of slow-release morphine are implanted subcutaneously in the dorsal scapular region of the rats to induce morphine dependence. On day-5 and -6, morphine withdrawal is induced by subcutaneous administration of 1.0 mg/Kg of naloxone, a general opioid antagonist. Compounds of the present invention or combinations thereof are administered (1.0, 5, 10, 20, 40 mg/Kg) to the rates 1 hour before naloxone injection. Ketamine (40 mg/Kg) is injected after test compound to induce sedation so as to avoid temperature fluctuation due to stress associated with restriction of their movement and attachment of thermistor probe to the their tails. All drug-related effects are compared to a vehicle control group which also receives ketamine. TST is monitored continuously for 35 minutes. The average TST measured 25, 30 and 35 minutes prior to naloxone injection is used to establish a baseline temperature. Hot flashes reduction is determined by evaluating the statistical differences between the baseline temperature and 15 minutes after naloxone treatment when the change in TST is observed to be maximum. Using the morphine-dependent rat model, the results will indicate that the compounds of the present invention abate naloxone-induced flush.

What is claimed is:

1. A method for treating, alleviating or controlling vasomotor symptoms comprising administering to a subject in need thereof a therapeutically effective amount of one or more norepinephrine/serotonin reuptake inhibitors (NRI/SRI) selected from a group consisting of nortriptyline, escitalopram, bupropion, nomifensine, nefazodone, and hydroxynefazodone in free or pharmaceutically acceptable salt form, wherein said one or more norepinephrine/serotonin reuptake inhibitors (NRI/SRI) are the sole active pharmaceutical agents in said method.

2. The method according to claim 1, wherein said norepinephrine/serotonin reuptake inhibitors is nortriptyline in free or pharmaceutically acceptable salt form.

3. The method according to claim 1, wherein said norepinephrine/serotonin reuptake inhibitors is in hydrochloride salt form.

4. The method of claim 1, wherein said norepinephrine/serotonin reuptake inhibitors is escitalopram, in free or pharmaceutically acceptable salt form.

5. The method according to claim 1, wherein said norepinephrine/serotonin reuptake inhibitors is bupropion, in free or pharmaceutically acceptable salt form.

6. The method according to claim 1, wherein said norepinephrine/serotonin reuptake inhibitors is nomifensine, in free or pharmaceutically acceptable salt form.

7. The method according to claim 1, wherein the subject is a female.

8. The method according to claim 1, wherein the subject is a premature, peri- or post-menopausal female wherein menopause is naturally, chemically or surgically induced.

9. The method according to claim 1, wherein the subject is a male undergoing naturally, chemically or surgically induced andropause.

10. The method according to claim 1, wherein said vasomotor symptom is hot flashes.

11. The method according to claim 1, wherein said norepinephrine/serotonin reuptake inhibitors is in a form of a pharmaceutical composition.

12. The method according to claim 1, wherein said norepinephrine/serotonin reuptake inhibitors is nefazodone, in free or pharmaceutically acceptable salt form.

13. The method according to claim 1, wherein said norepinephrine/serotonin reuptake inhibitors is hydroxynefazodone, in free or pharmaceutically acceptable salt form.

* * * * *